United States Patent [19]

Fedun

[11] Patent Number: 5,578,492
[45] Date of Patent: Nov. 26, 1996

[54] CELL CULTURE INSERT

[75] Inventor: Oresta N. Fedun, Wanaque, N.J.

[73] Assignee: Becton, Dickinson and Company, Franklin Lakes, N.J.

[21] Appl. No.: 671,091

[22] Filed: Jun. 28, 1996

Related U.S. Application Data

[63] Continuation of Ser. No. 538,053, Oct. 2, 1995, which is a continuation of Ser. No. 358,037, Dec. 15, 1994, which is a continuation of Ser. No. 630,116, Dec. 19, 1990.

[51] Int. Cl.$^6$ ............................................... C12M 3/06
[52] U.S. Cl. ......................... 435/297.5; 435/305.1; 422/101; 422/102
[58] Field of Search .......................... 435/297.1, 297.5, 435/289.1, 305.1, 240.241, 284–287, 296–301, 310, 311; 422/101, 102, 104; 210/238, 239, 249, 321.84, 476

[56] References Cited

U.S. PATENT DOCUMENTS

| | | | |
|---|---|---|---|
| 2,533,089 | 12/1950 | Brewer et al. | 435/297 X |
| 4,125,436 | 11/1978 | Liner | 435/287 |
| 4,349,632 | 9/1982 | Lyman et al. | 435/284 |
| 4,608,342 | 8/1986 | Nees | 435/240 |
| 4,657,867 | 4/1987 | Guhl et al. | 435/284 |
| 4,670,396 | 6/1987 | Bear et al. | 435/310 X |
| 4,686,190 | 8/1987 | Cramer et al. | 435/285 X |
| 4,748,124 | 5/1988 | Vogler | 435/240.241 |
| 4,871,674 | 10/1989 | Matsui et al. | 435/284 |
| 4,917,793 | 4/1990 | Pitt et al. | 435/284 X |
| 4,948,442 | 8/1990 | Manns | 156/73.1 |
| 5,139,951 | 8/1992 | Butz et al. | 435/284 |

FOREIGN PATENT DOCUMENTS 0239697  10/1987  European Pat. Off. .

Primary Examiner—Jeffrey Snay
Attorney, Agent, or Firm—Nanette S. Thomas

[57] ABSTRACT

A cell-supporting membrane separation device is provided in a cell culture insert to ease the use of conventional instrumentation for subsequent examination. The cell culture insert is provided with a microporous membrane forming the bottom wall as the cell culturing surface of the insert. The insert includes a support mechanism for holding the insert suspended in a selected position in a multi-well plate for culturing, and a break-away mechanism to separate the support mechanism from the membrane supporting portion of the insert, once the degree of cell culture activity has taken place. The break-away concept of the invention accommodates several different embodiments of insert with an appropriate break-away pattern.

2 Claims, 1 Drawing Sheet

CELL CULTURE INSERT

This is a continuation of copending application U.S. Ser. No. 08/538,053, filed on Oct. 2, 1995, which is a continuation of U.S. Ser. No. 08/358,037, filed on Dec. 15, 1994, which is a continuation of U.S. Ser. No. 07/630,116, filed on Dec. 19, 1990.

BACKGROUND AND DESCRIPTION OF THE INVENTION

This invention relates to cell culture inserts for insertion into multi-well plates for culturing cells. More particularly, this invention relates to such inserts which have placed on the bottom surface thereof a microporous membrane as the substrate for the cells being cultured. Even more particularly, this invention relates to such a cell culture insert having an arrangement for breaking away the bottom supporting portion of the membrane, once the cells have been properly developed, as required, so as to remove the supporting structure of the insert to eliminate its presence during subsequent examination of the cells having been developed in the insert.

That is, conventional instrumentation requires a certain dimension for examination of the cells, and eliminating this support mechanism of the cell insert allows much more ready examination of the cells without interference from the removed support structure.

Initially, when cell inserts were developed for multi-well plates, they were comprised of a plastic material with a membrane on the bottom surface thereof, for propagating cells. The inserts were placed in a conventional multi-well plate in the individual compartments therefor. Certain problems arise, however, with such structures in that the inserts have a tendency to move within the confines of the wells. Multi-well plates of the kind discussed here are similar to those shown and claimed in U.S. Pat. No. 4,349,632, for example, which is hereby incorporated by reference in its entirety.

Thus, structures were developed in the form of overhangs positioned around the upper edge of the cell inserts for suspending the cell inserts in the individual openings of the multi-well plates. Representative of such cell inserts are those described and claimed in European Patent Application No. 0239697 filed Oct. 31, 1986 and U.S. Pat. No. 4,871,674 issued Oct. 3, 1989.

While both of these structures have the effect of supporting the inserts in a suspended fashion in the multi-well plates so that the inserts do not move from one side to the other during propagation of the cells, they do interfere, in the sense of ultimate examination of the developed cells, because the supporting structures interfere with some conventional examination instrumentation. These instruments are expensive and not easily replaced. It is to this problem that this invention is particularly directed.

With this invention, by contrast, the bottom portion of the cell insert is arranged to be broken away. For this reason, the cell membrane itself with the developed cells on the surface thereof is supported in a separated structure of simplified configuration allowing for ready examination of the membrane and the cells developed thereon. There is no interference from the "superstructure" so to speak.

This arrangement is most important because it is necessary to maintain the suspension structure of cell inserts, as discussed above to avoid cultured cell damage. That is, with the use of a suspended microporous membrane, two cell types, for example, can be cultured, one of each side of the membrane in the same well. Without suspension, cells on the bottom surface of the membrane would be exposed to damage. The microporous membrane allows free passage of macromolecules, proteins and ions. As a result, the interactions of the two cell types can be studied without actual physical contact between the two cell populations in the suspended state of the insert. The growth environment mimics the in vivo state of cells being developed in vitro and may replace in vivo testing which has taken place in the past.

Moreover, because cells are being cultured on a microporous membrane substrate, they may be directly examined during the culturing. That is, direct viewing is possible of the living cells with phase contrast microscopy, during the actual cultivation period.

As purely representative of materials which may be utilized for the microporous membranes in the device of the invention include, for example, polycarbonate, polyethylene terephthalate. The porosity of the membrane is developed to allow for selective permeation, and as discussed above, the membrane material and/or the degree of porosity is developed to allow for direct viewing with phase contrast microscopy. The membranes are preferably transparent or translucent.

As a further feature of the advance in recent years of the desire to grow cells on porous culture inserts is so that a researcher has access to both the top and bottom surfaces of cells. Solid surfaces do not allow polar cells to grow and function in a normal in vivo fashion because polar cells, for example, have a distinct top and bottom surface. Use of culture inserts with a suspended porous membrane surface allows for this application. Moreover, and as mentioned above, co-culturing can take place with two or three different types of cells physically separated by the porous membrane and/or culture media. The membrane allows molecules and solution to pass the membrane but prevents direct cell contact between the cell types. Of course, as practitioners-in-the-art are aware, a third cell type may be cultured in the well into which the insert is placed.

It follows, that the support is necessary for obtaining all of the uses of the cell insert. Nevertheless, the support interferes with subsequent detailed examination of the cells. Thus, with the invention here, once The cells have been developed on the surface of the porous membrane, the structure immediately supporting the membrane may be broken away, in accordance with this invention, so that the cells may be readily examined in conventional instrumentation.

Other objects and advantages of this invention will be apparent from the following description, the accompanying drawings and the appended claims.

DETAILED DESCRIPTION OF THE INVENTION

Figure 1:
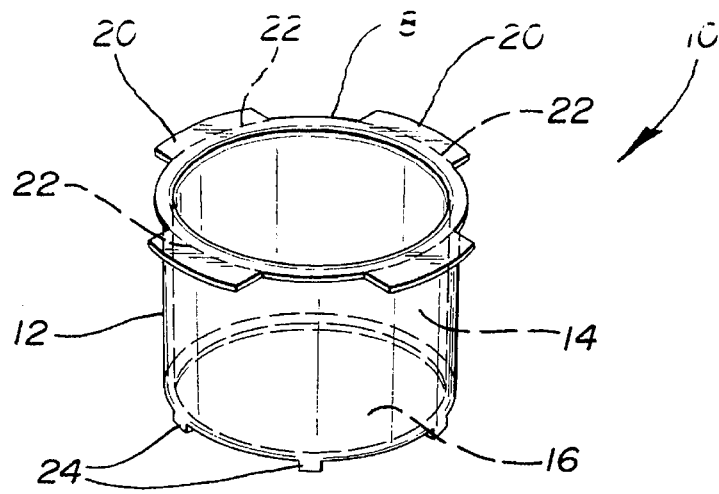
FIG. 1 is a perspective view of one embodiment of culture cell insert illustrating one form of break-away arrangement of the invention.

Referring to the drawings, in which like reference characters refer to like parts throughout the several views thereof, FIG. 1 shows one form of cell insert of the invention, generally designated 10 having a cylindrical vertical wall structure 12 defining a compartment 14. The bottom surface of compartment 14 is comprised of a microporous membrane 16, the surface of which is utilized to develop or culture cells, in accordance herewith and as discussed above in some detail. The outer edge of the membrane may be adhered to the bottom edge of wall 12 by heat or held between two snap-fit flanges (not shown). Insert 10 is supported on feet 24 when it is not supported from its overhanging spaced supports 20 once it is removed from the well. Spaced supports 20 extend from flange 18, which is integral with and extends from vertical wall 14 of device 10. The supports 20 are spaced to allow for insertion of probes or pipers during the culturing procedure.

As can be seen in FIG. 1, overhangs 20 may be broken away from the structure at weakened lines 22, once cell culturing has been completed. For this reason, the added dimension of overhangs 20 is removed and does not interfere with insertion of the insert 10 into appropriate conventional instrumentation for examination of the cultured cells on membrane 16. Nevertheless, with the embodiment shown in FIG. 1, insert 10, during insertion of insert 10 in the opening of a multi-well plate is supported on break-away flanges 20 so that no cells forming on the bottom surface of membrane 16 or the inside surface of the well are exposed to damage by inadvertent movement of insert 10 in a multi-well plate device.

Figure 2:
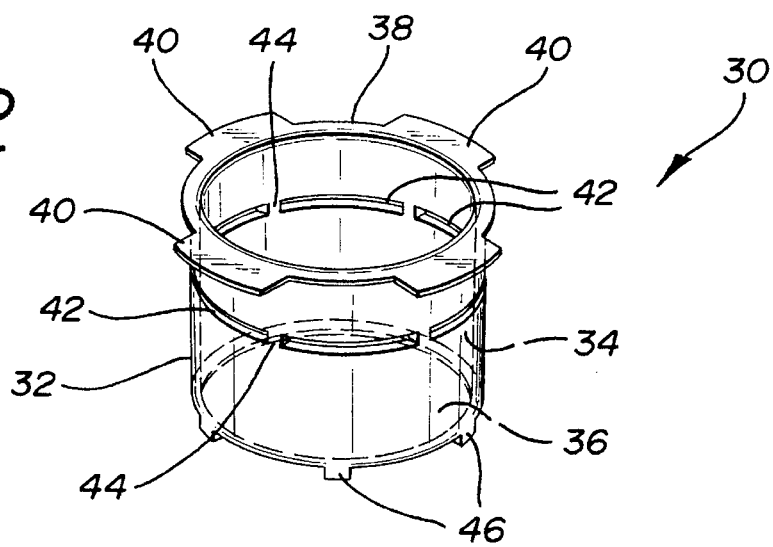
FIG. 2 is a perspective view of another embodiment of cell insert illustrating yet another break-away arrangement of the invention.

Referring now to FIG. 2, a second embodiment of culture cell insert 30 is shown with cylindrical vertical walls 32 defining a compartment 34. Again, this embodiment has a microporous membrane 36 forming the bottom surface of compartment 34 for the culturing of cells on the surface thereof. When the structure 30 is sitting on a flat surface, it is supported by feet or supports 46. Again, on the upper edge of vertical wall 32 is an annular flange 38 upon which is fixed a plurality of overhang supports 40 spaced around flange 38. These serve to support (or "hang") the insert 30 in the multi-well plate opening so that, again the insert 30 does not move during the culturing period of cells on membrane 36.

With this arrangement, a break-away weakened area 42, 44 is molded into the vertical wall 32. Thus, when culturing of cells on membrane 36 is completed, the wall 32 below the break-away area 42 may be broken away from the upper support structure leaving only the portion of wall 32 immediately adjacent the membrane 36. This allows easy insertion of the resulting broken away part into instrumentation for examining cells which have been cultured on membrane 36.

It should be understood that in both of these embodiments, because of the selected material utilized for the membranes 16 and 36, during actual culturing, the living cells may be viewed directly with phase contrast microscopy. This approach, was not possible with cell inserts having a solid plastic wall forming the bottom surface of the chamber 14 and 34. Of course, no cells were formed on the bottom surface of the bottom of the cell insert.

Figure 3:
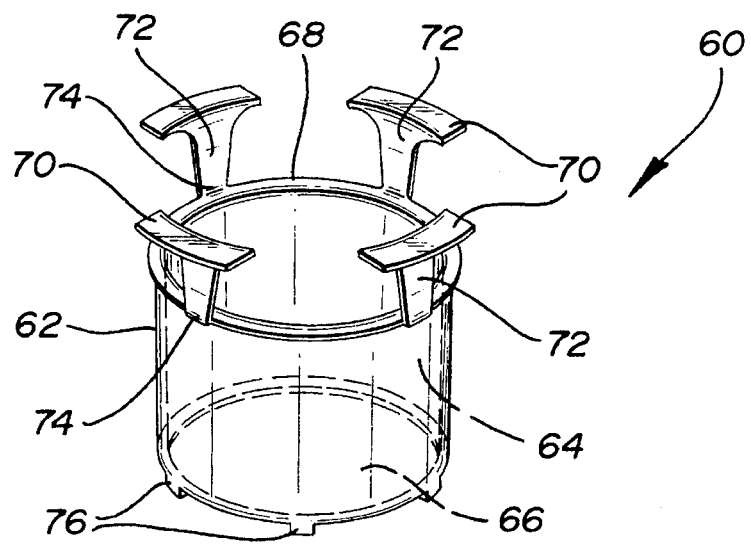
FIG. 3 is yet a further embodiment of cell insert of the invention showing a further break-away pattern arrangement for separating the supporting structure of the insert from the actual membrane.

Referring now to FIG. 3, yet a further embodiment of cell insert of the invention 60 is shown with an annular vertical wall 62 defining a chamber 64. In this embodiment, a microporous membrane 66 forms the bottom surface of the insert in the same manner as the previous embodiments discussed above. Also, this insert 60 has support feet 76 on the bottom surface thereof.

On the upper edge of the annular wall 62 is a flange 68. Extending upwardly from flange 68 are a plurality of vertical struts 72 for supporting overhangs 70 for supporting the insert 60 in a multi-well plate in the same manner as discussed with the previous embodiments. In this structure, the individual struts and overhangs 70, 72 may be broken away at weakened area 74 in order to remove these structures subsequent to the culturing of cells on membrane 66 so that the cultured cells may be readily examined on the membrane surface 66 in conventional instrumentation.

Thus, as will be appreciated from the above, there is provided in accordance with this invention, a cell insert arrangement with a break-away structure for removing unnecessary structure during subsequent examination of cells cultured on the porous membrane surface of the individual inserts. Because of this, the various embodiments of the device of the invention may be readily used in conventional instrumentation without the latter having to be replaced and/or modified.

As practitioners-in-the-art will understand, such instrumentation is extremely expensive and to avoid having to make modifications or replacements and still gain the advantage of being able to examine the cells cultured on the membranes, in accordance herewith, is a substantial advance. Moreover, the cell inserts of the invention may be comprised of simple moldable parts which can be mass produced from a variety of materials, including, for example, polyethylene, polystyrene, polyethylene terephthalate, and polypropylene. As will be understood further, by practitioners in the art, materials should be selected which will provide a small degree of resiliency for the purpose of providing ease of insertion of the inserts of the invention into multi-well plates and ease of break-away of the two individual parts forming the insert of the invention for subsequent examination of the developed cultured cells. Such resiliency provides, also, for ease of adhering the membrane to the bottom.

While the forms of apparatus herein described constitute preferred embodiments of the invention, it is to be understood that the invention is not limited to these precise forms of apparatus, and that changes may be made therein without departing from the scope of the invention which is defined in the appended claims. For example, whereas one form of insert is shown in cylindrical form in all three embodiments, thereof, it should be understood that other configurations of inserts may be utilized in the form of square or rectangular configurations, depending upon the configuration of openings in the multi-well plates or culture vessels being utilized.

What is claimed is:

1. A cell culture insert consisting of:

a body having a top end and a bottom end, vertical sidewalls extending from said top end to said bottom end to form a cell culture insert chamber;

a porous membrane positioned with said bottom end of said sidewall to form a bottom surface of said chamber;

a plurality of overhanging flanges extending radially outward from said top end, spaced apart from each other and extending beyond said sidewall; and weakened regions between said plurality of flanges and said top end whereby said flanges are broken away from said top end of said sidewall.

2. A cell culture insert consisting of:

a body having a top end surface and a bottom end surface, vertical sidewalls extending from said top end surface to said bottom end surface to form a cell culture insert chamber;

a porous membrane positioned with said bottom end surface, a plurality of vertical struts extending upwardly from said top end surface and comprising an upper edge surface;

a flange extending radially outwardly from said upper edge surface of each vertical strut; and a weakened connection between each vertical strut and said top end surface whereby each strut is capable of being broken away from said top surface.

* * * * *